United States Patent [19]

Vogel

[11] Patent Number: 5,527,340
[45] Date of Patent: Jun. 18, 1996

[54] SURGICAL INSTRUMENT WITH GRIPPING PORTION

[75] Inventor: Max Vogel, Neuhausen am Rheinfall, Switzerland

[73] Assignee: S & T Marketing AG, Neuhausen, Switzerland

[21] Appl. No.: 198,211

[22] Filed: Feb. 17, 1994

Related U.S. Application Data

[63] Continuation of Ser. No. 511,763, Apr. 20, 1990, abandoned.

[51] Int. Cl.$^6$ .................................................... A61B 17/00
[52] U.S. Cl. ........................... 606/205; 606/174; 128/751
[58] Field of Search ........................... 606/174, 205–211; 294/99.2, 100; 128/750–755

[56] References Cited

U.S. PATENT DOCUMENTS

| | | | |
|---|---|---|---|
| 943,263 | 12/1909 | Moraweck | 606/207 |
| 2,406,393 | 8/1946 | Neugass | 606/210 |
| 2,665,692 | 1/1954 | L'Esperance | 606/211 |
| 4,610,252 | 9/1986 | Catalano | 606/207 |
| 4,693,246 | 9/1987 | Reimels | 606/148 |

Primary Examiner—Stephen C. Pellegrino
Assistant Examiner—William W. Lewis
Attorney, Agent, or Firm—Bachman & LaPointe

[57] ABSTRACT

A surgical instrument, in particular microsurgical scissors or cutters or tweezers or forceps, with a gripping portion and at least one gripping surface which extends over at least a section of the gripping portion and which affords enhanced friction in comparison with the adjacent sections of the instrument, is improved in that the gripping surface is in the form of a roughening with small, juxtaposed raised portions and depressed portions of different dimensioning and with an arrangement which is irregular in respect of dimensioning.

8 Claims, 1 Drawing Sheet

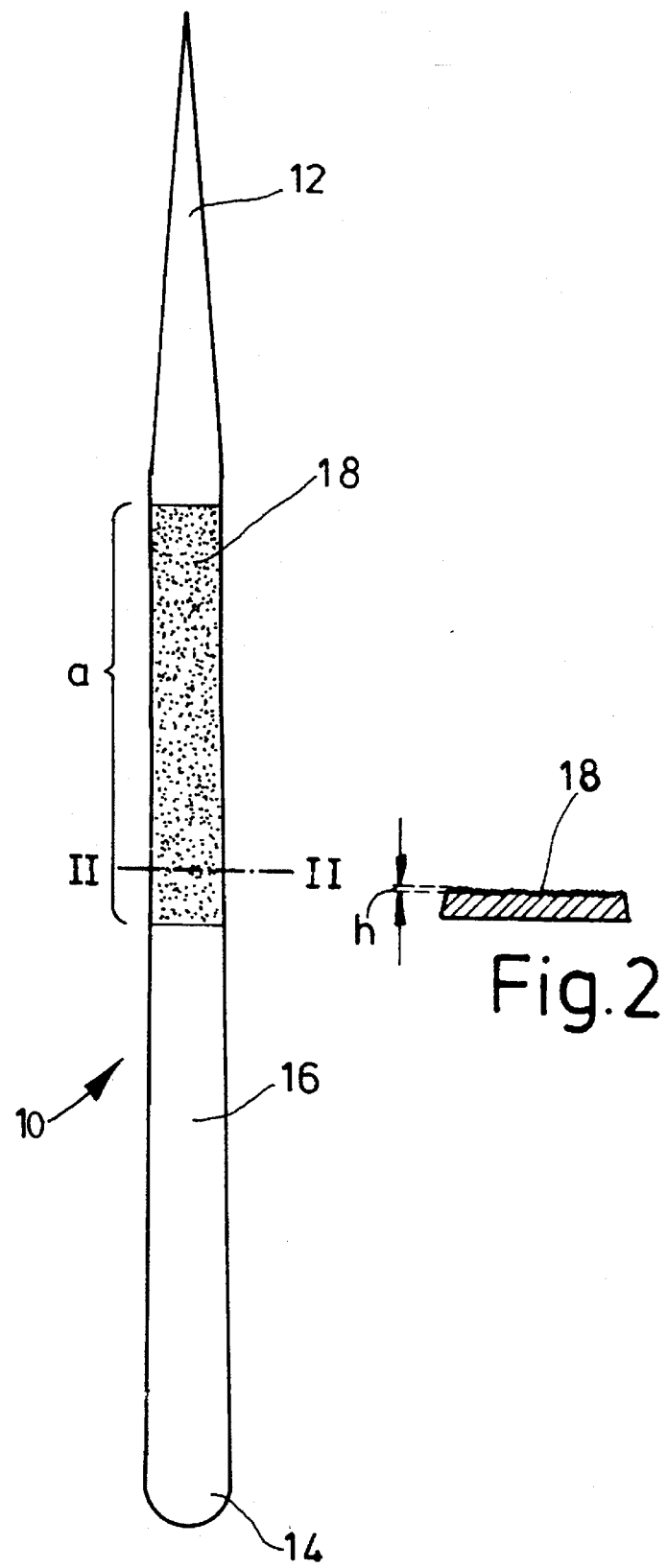

SURGICAL INSTRUMENT WITH GRIPPING PORTION

This is a continuation of application Ser. No. 511,763 filed on Apr. 20, 1990, now abandoned.

BACKGROUND OF THE INVENTION

With a gripping portion and at least one gripping surface which extends over at least a section of the gripping portion and which affords enhanced friction in comparison with the adjacent sections of the instrument.

In regard to surgical instruments such as tweezers or forceps, vessel dilators, clamping forceps, scissors or cutters, needle holders, arteriotomy clamps etc., a distinction is made between flat and round grip instruments; in a flat grip instrument, for example, in regard to a pair of tweezers, the legs thereof, the gripping portion, is of rectangular cross-section, whereas in the case of a round grip instrument the gripping portion is of a semicircular configuration.

In the development of surgical instruments, in particular for microsurgical purposes, there is the requirement that they should be continuously refined from the ergonomic point of view; the aim is to the effect of relieving the load on the hand of the operator while working, and increasing the level of operating comfort. For that purpose, for example in relation to flat grip instruments, the gripping portions were provided at their outside surface or surfaces with gripping surfaces which extend in the longitudinal direction of the instrument and the length of which is determined from variations in spacing, arising out of the operation technique, in respect of the hand of the surgeon relative to the area of operation. To provide for safe and secure handling of the instruments, the gripping surfaces, which in the case of flat grip instruments extend generally over the entire width of the gripping portion while in the case of a round grip instrument they extend on the circumferential surface thereof, have different roughening configurations in the form of holes or grooves which extend transversely with respect to the longitudinal axis of the gripping portions and which are produced by a cutting machining operation; in that case a finger pad on the hand of the user can bear against the grooves while using the instrument.

Particularly in relation to round grip instruments, it is known for the circumference thereof to be provided with mutually crossing grooves so as to produce square or rectangular raised surface portions, depending on the respective groove spacing used.

With gripping surface configurations of that kind, an equilibrium position was produced in the hand of the surgeon by virtue of a particular design configuration of the instruments, while the instrument also made it possible to go easy on the hand muscle strength of the operator by virtue of a reduction in weight and possibly with use-specific fine tuning of the pressure of spring elements. The applicants developed microsurgical instruments of that kind, which afford a high level of operating comfort, and such instruments are described as state of the art in the applicants' sales publications which are available to the public.

In relation to operations of medium and prolonged duration, in particular operations of microsurgical nature, an equilibrium or balance position, a low weight and spring pressures which are set to a minimum value, as far as the inventors are aware, are not crucial on their own in regard to reducing fatigue phenomena in respect of the hand of a surgeon and postponing the occurrence thereof, by virtue of a suitable reduction in the muscle force which is thereby otherwise required.

On the contrary, the extent and the time of occurrence of fatigue phenomena are also determined by the level of the local compression loading on the finger pads and in relation thereof a more or less pronounced level of pressure sensitivity, which are not to be eliminated in regard to instruments of the above-described kind, by very fine mechanical processing such as rounding, polishing and coating of the grooves and raised surface portions, and by wearing surgical gloves.

SUMMARY OF THE INVENTION

In consideration thereof, the inventor set himself the object of providing surgical instruments of the king discussed above in which the level of local compression loading and pressure sensitivity on the finger pads is reduced in comparison with the known gripping surfaces, and safe and secure handling of the instrument is guaranteed.

That object is attained in that the gripping surface is in the form of a roughening with small closely juxtaposed raised portions and depressed portions of different dimensioning and with an arrangement which is irregular in respect of dimensioning. In that connection the roughness depth is advantageously to be less than 0.5 mm, preferably less than 0.2 mm.

In accordance with further features of the invention, the surface is to be formed by mechanical roughening or by chemical roughening or by electrical roughening; a cutting surface machining operation does not achieve the purpose which the inventor has in mind.

It is in accordance with the invention for the section of the gripping portion, which is provided for the gripping surface, to be degreased and then roughened up, and coated with aluminum oxide using plasma spraying.

Surprisingly gripping surface configurations of the kind according to the invention markedly reduce the pressure on the finger pads and pressure sensitivity during use of a surgical instrument so that fatigue phenomena are markedly reduced and further delayed in time.

BRIEF DESCRIPTION OF THE DRAWINGS

Further advantages, features and details of the invention will be apparent from the following description of a preferred embodiment and with reference to the drawings in which:

FIG. 1 is a plan view of a pair of microsurgical tweezers with a gripping surface of a configuration in accordance with the invention, and FIG. 2 is a view in section in FIG. 1 on an enlarged scale, taken along line II—II therein.

DETAILED DESCRIPTION

Gripping surfaces of the kind as described and claimed hereinafter may obviously also be used on the gripping portions of other surgical instruments such as vessel dilators, clamping forceps, scissors or cutters, needle holders, arteriotomy clamps and holders of counter-pressure ties.

FIG. 1 shows a plan view of a pair of tweezers 10 in the form of a flat grip instrument with a tip 12 and a gripping portion 16 having a rounded end 14. Adjoining the tip 12 which is conical in plan view is a roughened gripping surface 18 which extends transversely over the entire gripping portion 16 and which is of a length a. The surface structure of the gripping surface has small, closely juxtaposed raised portions and depressed portions of different dimensioning and in an arrangement which is irregular in respect of dimensioning. The measurement of the maximum depth of roughness is identified by h in FIG. 2 and measures about 0.2 mm.

That roughness is produced by mechanical, chemical or electrical roughening. Mechanical roughening is effected by means of blasting with granular material such as glass blasting. Chemical roughening can be effected by etching while electrical roughening can be effected by means of spark erosion.

In those roughening processes, the size and height h of the raised portions and depressed portions as well as their arrangement and distribution remain variable in dependence on the granular material used, the acid and etching duration or in accordance with the surface configuration of the erosion electrode, so that the best possible surface structure can be provided according to the intended conditions of use for each surgical instrument.

I claim:

1. A surgical instrument, in particular microsurgical scissors or cutter or tweezers or forceps, which comprises a gripping portion comprising an elongated body portion for gripping by the hand of a user and at least one gripping surface which extends over at least a section of the gripping portion and which affords enhanced friction in comparison with the adjacent sections of the instrument, wherein the gripping surface is in the form of a roughening with small, juxtaposed raised portions and depressed portions of different dimensioning and with an arrangement which is irregular in respect of dimensioning over the entire gripping surface, wherein said gripping surface is formed by electrical roughening by spark erosion.

2. An instrument according to claim 1 having a roughness depth less than 0.5 mm.

3. An instrument according to claim 1 having a roughness depth less than 0.2 mm.

4. An instrument according to claim 1 having a roughness depth less than 0.1 mm.

5. A method for forming a surgical instrument, in particular microsurgical scissors or cutters or tweezers or forceps, said instrument having a gripping portion for gripping by the hand of a user and at least a section of the gripping portion and which affords enhanced friction in comparison with adjacent sections of the instrument, which comprises roughening the gripping surface to form juxtaposed raised portions and depressed portions of different dimensioning and with an arrangement which is irregular in respect of dimensioning over the entire gripping surface, said roughening being by electrical roughening by spark erosion.

6. A method according to claim 5 including the step of roughening the gripping surface to a roughness depth of less than 0.5 mm.

7. A method according to claim 6 including the step of roughening the gripping surface to a roughness depth of less than 0.2 mm.

8. A method according to claim 6 including the step of roughening the gripping surface to a roughness depth of less than 0.1 mm.

* * * * *